United States Patent [19]

Kudo et al.

[11] Patent Number: 5,734,091
[45] Date of Patent: Mar. 31, 1998

[54] METHOD OF MANUFACTURING NITROGEN OXIDE SENSOR, AND NITROGEN OXIDE SENSOR MANUFACTURED BY THE METHOD AND MATERIAL THEREFOR

[75] Inventors: Shuzo Kudo, Ikoma; Hisao Ohnishi, Osaka; Hisashi Sakai, Kyoto, all of Japan

[73] Assignee: Osaka Gas Co., Ltd., Osaka, Japan

[21] Appl. No.: 805,037

[22] Filed: Feb. 21, 1997

[30] Foreign Application Priority Data

Feb. 21, 1996 [JP] Japan .................... 8-033296

[51] Int. Cl.⁶ .............. G01N 29/00; G01N 27/04; G01N 27/12; H01C 7/00
[52] U.S. Cl. .............. 73/23.2; 73/31.01; 73/23.32; 73/31.06; 422/98; 422/94; 427/126.1; 338/34; 29/25.01; 436/137; 324/71.5
[58] Field of Search .................. 73/23.2, 23.31, 73/31.01, 31.06, 23.32; 427/125, 126.1, 126.3; 422/98, 94, 88; 338/34; 29/25.01; 324/71.5; 436/137; 340/633–4

[56] References Cited

U.S. PATENT DOCUMENTS

| | | | |
|---|---|---|---|
| 4,221,827 | 9/1980 | Parry et al. | 427/125 |
| 4,224,280 | 9/1980 | Takahama et al. | 422/98 |
| 4,251,225 | 2/1981 | Handa et al. | 23/232 E |
| 4,381,922 | 5/1983 | Frey et al. | 422/98 |
| 4,454,494 | 6/1984 | Williams et al. | 338/34 |
| 4,587,104 | 5/1986 | Yannopoulos | 422/94 |
| 4,658,632 | 4/1987 | Sasaki | 73/23 |
| 4,722,905 | 2/1988 | Honeybourne et al. | 436/151 |
| 4,794,323 | 12/1988 | Zhou et al. | 324/71.5 |
| 4,860,573 | 8/1989 | Barendz et al. | 73/23 |
| 4,944,273 | 7/1990 | Baresel et al. | 123/440 |
| 4,977,658 | 12/1990 | Awano et al. | 29/25.01 |
| 5,086,286 | 2/1992 | Yasukawa et al. | 338/34 |
| 5,222,388 | 6/1993 | Sinha et al. | 73/23.2 |
| 5,389,340 | 2/1995 | Satake | 422/98 |
| 5,397,541 | 3/1995 | Post | 422/98 |
| 5,563,331 | 10/1996 | Von Helmott et al. | 73/31.05 |
| 5,618,496 | 4/1997 | Hasumi et al. | 422/90 |

OTHER PUBLICATIONS

Supercond. Sci. Technol. 7 (1994). pp. 367–371; Growth and Characterization of Bulk-Textured $Bi_2Sr_2Ca_{1-x}Y_xCu_2O_8$ By the Float Zone Technique; P. Murugakoothan, R. Jayavel, C.R. Venkateswara Rao, C. Subramanian and P. Ramasamy, Crystal Growth Centre, Anna University, Madras 600 0245 India, Jan. 10, 1994.

Japanese Journal of Applied Physics, vol. 27, No. 8, Aug. 19, 1988, pp. L1432–L1434, Electrical and Magnetic Properties in $Bi_2Sr_2Ca_{1-x}Y_xCu_2O_{8+\delta}$; Noburu Fukushima, Hiromi Niu and Ken Ando, Toshiba Corporation, Research & Development Center, Saiwai-ku, Kawasaki 210, Jul. 22, 1988.

(List continued on next page.)

*Primary Examiner*—Hezron E. Williams
*Assistant Examiner*—J. David Wiggins
*Attorney, Agent, or Firm*—Felfe & Lynch

[57] ABSTRACT

A method of manufacturing a nitrogen oxide sensor for detecting a nitrogen oxide to be used in the field of e.g. reducing or decomposing nitrogen oxides, as well as such sensor and material suitable for manufacturing the sensor are disclosed. For manufacturing the sensor material, a precursor containing components for constituting the sensor material in a predetermined equivalent ratio of stoichiometry between chemical elements is prepared. First, the precursor is subjected to sintered to a preliminary sintering step. Then, the resultant sintered material is subjected to at least two cycles of main sintering step at 815° to 848° C. (T1) with an intermediate grinding step of the sintered material therebetween, thus obtaining the gas detecting portion comprised mainly of oxide compound having a composition represented by:

$$Bi_2Sr_2YCu_2O_{8+y}$$

$(0 \leq y \leq 1)$
and having the 2212 phase of crystal structure.

6 Claims, 4 Drawing Sheets

OTHER PUBLICATIONS

J. Am. Ceram. Soc., 76[3] pp. 635–640 (1993); High-Temperature Electrical Properties of the $Bi_{2.1}Sr_{1.9}(Ca_{1-x}Y_x)Cu_2O_x$ Solid Solution; Byungsun Hong and Thomas O. Mason, Science & Technology Center for Superconductivity, Dept. of Materials Science & Engineering, Northwestern University, Evanston, Illinois 60208.

Japanese Journal of Applied Physics, vol. 28, No. 5, May 1989, pp. L784–L786; Periodicity Change in Structural Modulation in $Bi_2Sr_2Ca_{1-Y}RE_YCu_2O_{8+\delta}$ RE=Y, Nd) System, Hiromi Niu, Noburu Fukushima, Shiro Takeno, Shin-ichi Nakamura and Ken Ando, Toshiba Corporation, Research & Development Center, Saiwai-ku, Kawasaki 210, Apr. 13, 1989.

METHOD OF MANUFACTURING NITROGEN OXIDE SENSOR, AND NITROGEN OXIDE SENSOR MANUFACTURED BY THE METHOD AND MATERIAL THEREFOR

BACKGROUND OF THE INVENTION

1. Field of the Invention

The present invention relates to a method of manufacturing a nitrogen oxide sensor for detecting a nitrogen oxide to be used in the field of e.g. reducing or decomposing nitrogen oxides, and the invention relates also to such sensor and material suitable for manufacturing the sensor.

2. Description of the Related Art

Nitrogen oxides present in the combustion exhaust gases emitted from an engine, a boiler or the like should be eliminated or reduced as they cause air pollution. Hence, there is an urgent demand for a sensor capable of high-precision measurement of nitrogen oxide concentration in exhaust gas.

As the conventional methods of measuring a concentration of nitrogen oxide in exhaust gas, there are known those based on the chemiluminescence method, infrared absorption method, ultraviolet absorption method, controlled potential electrolysis method, controlled potential and so on. In addition to these, as a further improved sensor capable of solving problems of the above-listed types, there has also been proposed a sensor using a superconducting material.

And, as the last-mentioned type of sensor, the present inventors, i.e. Kudo et al., proposed use of a material represented by the following formula and having 2212 crystal structure. Namely;

$$Bi_2Sr_2(Ca_{1-x}Y_x)Cu_2O_{8+y} \qquad \text{(formula 4)}$$

$(0 \leq x < 1; 0 \leq y \leq 1)$

The sensor having the above-specified structure has good sensitivity to nitrogen oxides and also reversible sensitivity which is another essential requirement of a sensor (Japanese patent application Hei. 5-160985).

Concerning sintering of such oxide compound as above, conventionally the main sintering step was done in the vicinity of the melting point of the material.

According to the conventional belief, the melting point of such oxide compound rises with increase in its Y content (see "Superconductor Science & Technology, 7[6] (1994) (U.S.A.) p367–371). For instance, in the case of the particular oxide compound of the above formula 4, the melting point is around 880° C. when x=0. Whereas, it is elevated to around 950° C. when x=1.

Accordingly, if the ratio of Y was to be increased relative to Ca (typically for x=1), the high temperature (i.e. near 930° C.) was employed as the sintering temperature (see "Japanese Journal of Applied Physics. 27 [8] 1988-8. (Japan) P1432–1434, reference 2 hereinafter). In this reference document, indeed, the sintering temperature is set at 855° C. in case x=0; and the sintering temperature is set to 920° C. in case complete Y-substituted compound is made, i.e. x=1.

In general, in order for a sensor to be practically useful, the sensor should meet three requirements as follow.

(1) good selective sensitivity to a particular target gas component;

(2) good reversible sensitivity for immediate return to the zero point, i.e. the point of origin, as soon as the concentration of the target gas component becomes 0 (zero); and (3) good durability against aging.

2

In the above respects, as far as the requirement (1), i.e. selective sensitivity is concerned, as described hereinafter, it has been established that the oxide compound represented by a following formula 5 and having the crystal structure of 2212 phase is best preferred.

$$Bi_2Sr_2YCu_2O_{8+y} \qquad \text{(formula 5)}$$

$(0 \leq y \leq 1)$

However, those skilled in the art have found it difficult to obtain material having the 2212 phase and found it even more difficult to obtain the 2212 phase in a sufficiently large proportion (see "Journal of the American Ceramic Society" 76[3] 1993 (U.S.A.) p635–640). Namely, this reference describes that there exists a limit in the Y-substituted solid solution at the Ca site at 80% approximately and FIG. 1 accompanying this reference illustrates that the change in the C-axis length reaches its bottom at the above-mentioned limit and remains saturated thereafter.

Further, if the material contains also any other phase than the 2212 phase or any other crystal systems in a mixed state, as will be detailed later, such multi-phase or multi-system material, if used as a sensor, will be unsatisfactory not only in the reversible sensitivity (the ability to immediately return to its point of origin) but also in the durability against aging. That is, this sensor, after use for an extended period of time, tends to suffer such problem as deterioration in its sensitivity.

In view of the above, a primary object of the present invention is to provide a method of manufacturing improved nitrogen oxide sensor which is superior not only in the aspects of the sensitivity to nitrogen oxide and reversible sensitivity but also in the other important sensor requirement of the durability against aging (i.e. stable sensing characteristics). Another object of the invention is to provide a nitrogen oxide sensor having such superior characteristics. A still further object of the invention is to provide material suitable for manufacturing such improved nitrogen oxide sensor.

SUMMARY OF THE INVENTION

For accomplishing the above-noted object, according to one aspect of the present invention, in a method of manufacturing a nitrogen oxide sensor having a gas detecting portion formed of sensor material having electrical property thereof variable in response to concentration of nitrogen oxide present in a gas and electrodes electrically connected to the gas detecting portion, the method comprises:

a first step of obtaining a precursor containing components for constituting the sensor material in a predetermined equivalent ratio of stoichiometry between chemical elements;

a second step of obtaining a preliminary sintered material by subjecting the precursor obtained from the first step to a preliminary sintering; and a third step of subjecting the preliminary sintered material resulting from the second step to at least two cycles of main sintering step at 815° to 848° C. (T1) with an intermediate grinding step of the sintered material therebetween, thus obtaining the gas detecting portion comprised mainly of oxide compound having a composition represented by:

$$Bi_2Sr_2YCu_2O_{8+y} \qquad \text{(formula 6)}$$

$(0 \leq y \leq 1)$ and having the 2212 phase of crystal structure.

In the above method, for obtaining the sensor material for constituting the gas detecting portion, the first through third steps described above are effected. The first and second steps are conventionally practiced steps, and the present invention is characterized by the third step, i.e. the main sintering step.

Namely, according to this method of the present invention, in the main sintering step, the sintering temperature is chosen to be 815° to 848° C. (T1) which is markedly lower than the conventionally practiced sintering temperature range (e.g. 920° to 930° C. approximately). The sintering atmosphere may be rare gas or nitrogen gas atmosphere containing oxygen. The above temperature range is 80° to 100° C. lower than the conventional sintering temperature which was set near the melting point of the material. The advantageous effect of such lowered sintering temperature range was newly found by the present inventors.

Also, this main sintering step is effected for at least two cycles, with an intermediate grinding step of the sintered material therebetween. By effecting the sintering step for a plurality of cycles, the resultant material obtains a greater degree of homogeneity.

As the result of the above, there may be reliably and readily obtained the target oxide compound having the composition represented by the above formula 6 and comprised mainly of the 2212 phase.

Figure 1:
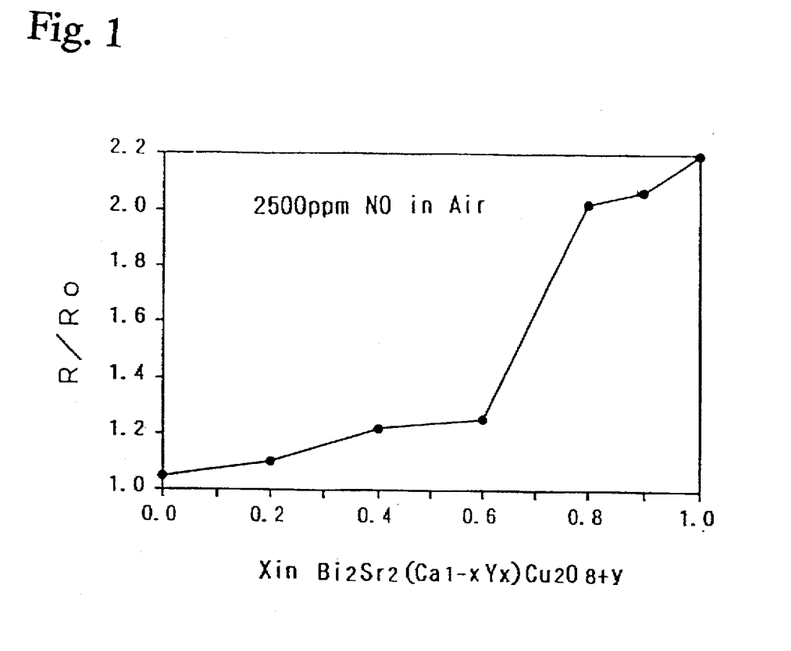
FIG. 1 is a graph showing sensitivity to Bi—Sr—Ca—Y—Cu—O system nitrogen oxide material.

The sensing characteristics of this oxide compound to nitrogen oxide is illustrated in FIG. 1. This figure graphically shows the sensitivity ($R/R_0$) relative to nitrogen oxide of composite oxide materials all represented by a following general formula 7:

$$Bi_2Sr_2Ca_{1-x}Y_xCu_2O_{8+y} \quad \text{(formula 7)}$$

($0 \leq x \leq 1$; $0 \leq y \leq 1$).

In the graph, the horizontal axis represents the ratio between Y and Ca (Y/Ca), and x=0 denotes a material having only Ca with total absence of Y. Conversely, x=1 denotes a material having only Y with total absence of Ca. The vertical axis represents a ratio between the value of electrical resistance of the material ($R_0$) in air as a reference gas and the value of resistance (R) thereof in gases including air together with 2500 ppm of NO.

As may be apparent from this figure, the sensor material having the particular structure employed by the present invention (i.e. (Y/Ca)=(1/0)) shows the highest sensitivity to the nitrogen oxide, so that this sensor material may reliably detect even a small change in the nitrogen oxide concentration as an associated change in the electric resistance thereof.

Figure 2:
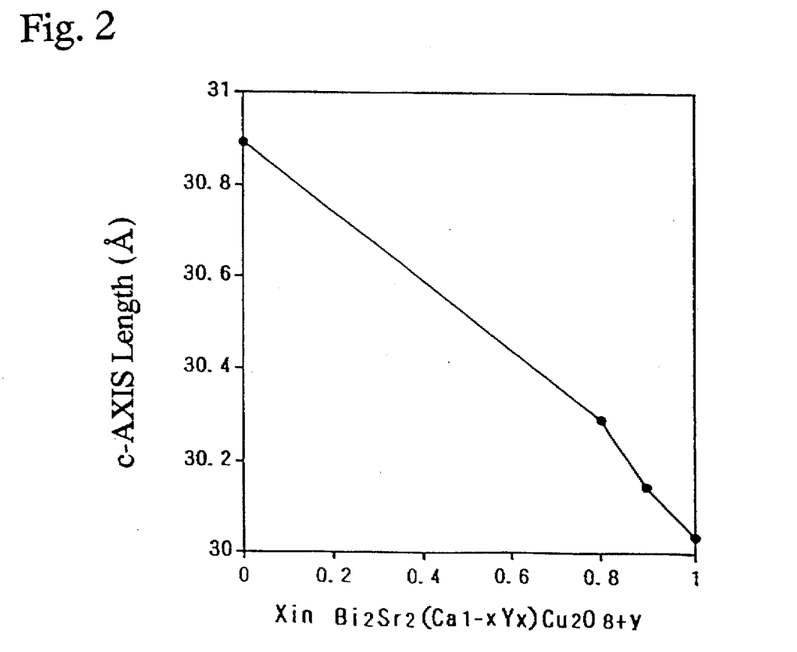
FIG. 2 is a graph illustrating the correlation between Y content in oxide compound and the c-axis length of the crystal lattice.

FIG. 2 illustrates gradual change in the c-axis length in the crystal lattice where oxide compound is obtained from the precursor having the material composition represented by the above general formula 7 by the same method as employed by the present invention.

As shown, there may be observed monotonous decrease in the c-axis length with increase in Y content. By this, it may be reasonably believed that the particular material represented by the formula 6 and having the 2212 phase is formed indeed. Whereas, there is not observed such monotonous decrease in the c-axis length in the case of the convention (see FIG. 3 of "Japanese Journal of Applied Physics", 28[5] 1989-5. (Japan) p784–876 as well as FIG. 2 of Reference 2). Accordingly, the above-described method is suitable for obtaining the target material and this was newly discovered by the present inventors.

Figure 3:
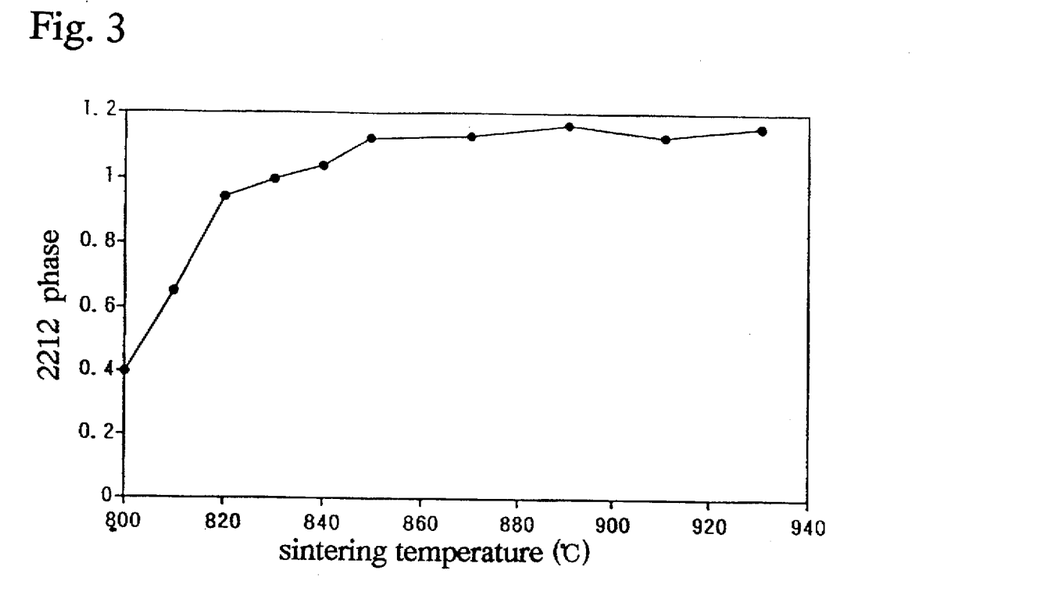
FIG. 3 is a graph illustrating the correlation between the sintering temperature and the ratio of 2212 phase.
Figure 4:
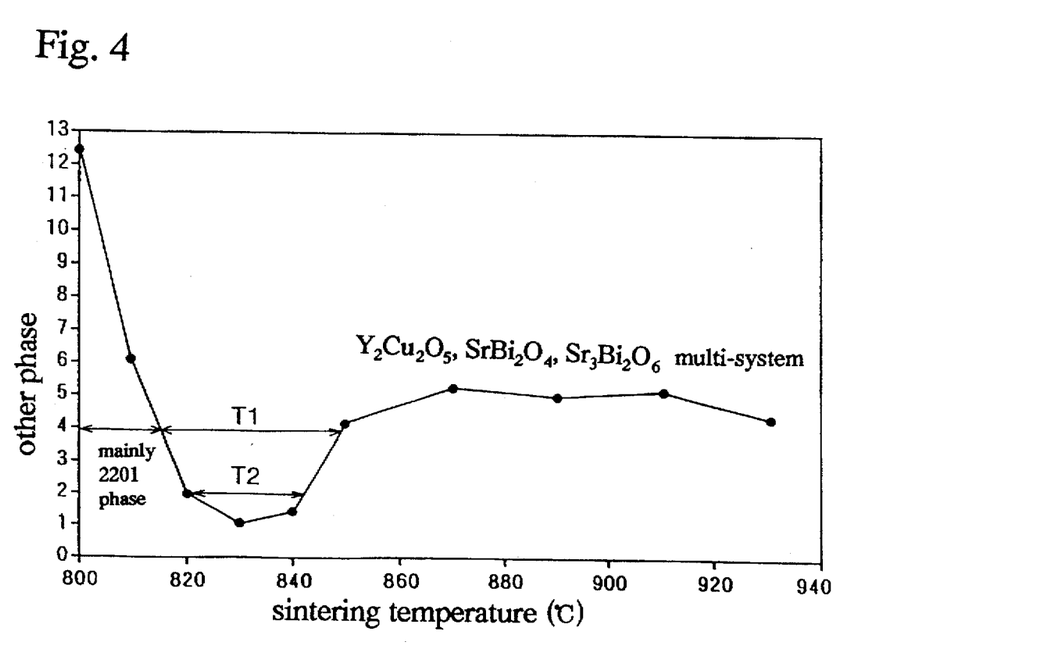
FIG. 4 is a graph illustrating the relationship between the sintering temperature and multi-system state of the sintered material.

Next, the newly discovered correlation between the sintering temperature employed in the main sintering step and the resultant difference in the phase of the material will be described in greater details with reference to FIGS. 3 and 4. These figures are intended to be considered in conjunction with each other, in each of which the horizontal axis represents the sintering temperature (°C.). Also, the vertical axis in each figure represents the sum of diffraction peak intensities, by an X-ray diffraction analysis using Cu—Kαray, of predetermined crystal phases of diffraction angles ranging between 5 and 65 degrees, the sum of measured peak intensity values being standardized relative to the sum of peak intensities of material sintered at 830° C. FIG. 3 shows the change in the sum values concerning the 2212 phase, the subject of the present invention. FIG. 4 shows the sums concerning the other phases or systems than the 2212 phase. Therefore, in FIG. 3, the greater the value, the larger the ratio of the 2212 phase, and the opposite is true in FIG. 4.

As may be understood from FIG. 3, the ratio of the 2212 phase increases with rise in the sintering temperature and this rate becomes substantially saturated above 850° C. approximately. On the other hand, as may be understood from FIG. 4, although the ratio of the 2212 phase first increases with rise in the sintering temperature, the rate of increase begins to drop across the transition point of 830° C., after which a certain multi-system state is developed and maintained. Here, it was confirmed, through a separate analysis, that this multi-system state consists of un-wanted crystal systems or compounds of: $Y_2Cu_2O_5$, $SrBi_2O_4$ and $Sr_3Bi_2O_6$.

Therefore, if the 2212 phase, the target phase of the present invention, is to be obtained in a stable manner, it is essential that the main sintering temperature be set to the range of 815° to 848° C. (T1).

If the sintering temperature is lower than 815° C., the 2201 phase, rather than the target 2212 phase, tends to grow. Whereas, if the sintering temperature is higher than 848° C., the above-described multi-system state tends to develop. Namely, when the sintering temperature exceeds 848° C., this makes Y-substitution into the 2212 phase crystal structure more difficult, thus making it difficult to grow the structure represented by the formula 6 and having the 2212 phase. Then, any remaining Y which was not incorporated into the target crystal structure by the solid solution process forms the foreign, i.e. unwanted, crystal compounds, thus resulting in the multi-system state.

The multi-system state is disadvantageous for the following reason. Namely, adsorption of nitrogen oxide to the foreign crystal systems involves certain chemical reactions. With increase in the ratio of the foreign crystal systems, this inevitably increases the possibility of these foreign systems being serially incorporated into the electric circuit constituted by the 2212 phase. As a result, in comparison with a gas detecting portion having an electric circuit comprised of the 2212 phase alone, the gas detecting portion having will be unsatisfactory in the sensor requirements of its ability to return to the point of origin and durability against aging as well.

More preferably, the main sintering step is effected for at least two cycles at a more-focused temperature range of 820° to 845° C. (T2) for a period longer than 30 (thirty) hours in each cycle.

With this more-focused setting of the sintering temperature of 820° to 845° C. (T2), as may be understood from FIG. 4, the ratio of the target 2212 phase may be further increased to such a degree that the resultant material will consist substantially solely of the 2212 phase.

As also shown, the best sintering temperature is 830° C. Yet, if the sintering temperature range is set between 828° and 835° C., the ratio of the non-target phase or systems other than the target 2212 phase may still be limited to be not higher than 1.5 times of that of the material sintered at 830° C. On the other hand, the sintering extended for a period longer than 30 hours results in better homogeneity of the sintered material.

As described above, by employing the method of the invention, it is possible to obtain the material represented by the formula 6 and comprised mainly of the 2212 phase, without inviting formation of multi-phase or multi-system. Next, the durability of this material will be described with reference to FIG. 5.

Figure 5:
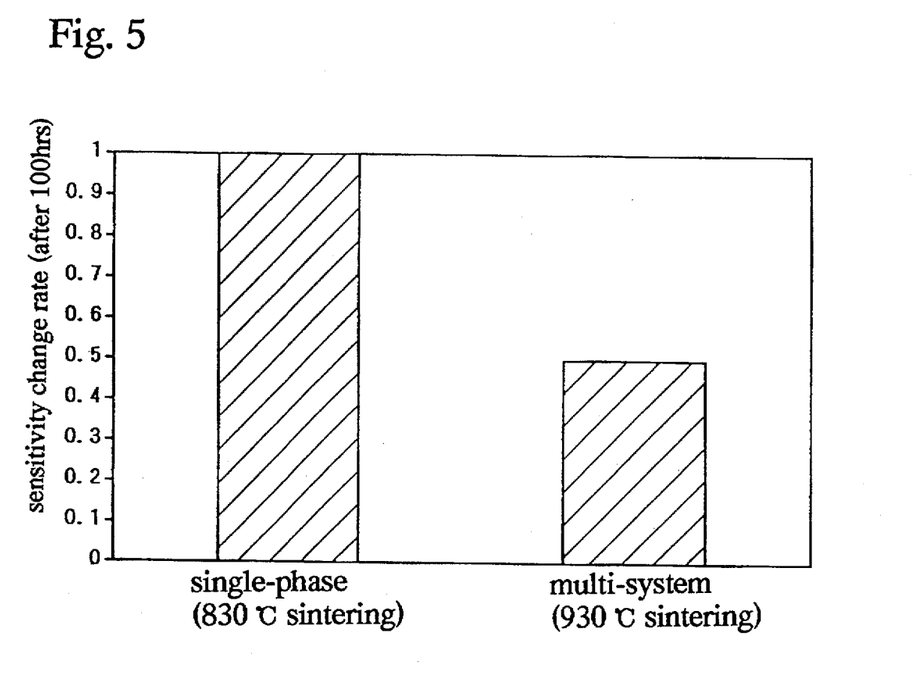
FIG. 5 is a graph illustrating the relationship between the multi-system state of sintered material and change in its sensitivity due to aging.

FIG. 5 illustrates the rate of change in the sensitivity of the above material after 100 hour exposure thereof to a simulated exhaust gas containing 300 ppm of NO. In this figure, the 'single-phase material' denotes the material subjected to the main sintering step at 830° C., i.e. the material according to the present invention. Also, the 'multi-system material' denotes the further material subjected to a main sintering step at 930° C., i.e. the conventional material.

In this durability test, there was employed the simulated exhaust gas.

Specifically, the simulated gas for a durability test contained NO, $O_2$, $CO_2$, CO, $H_2$, $CH_4$, $C_2H_8$, $i-C_4H_{10}$, $H_2O$ and $SO_2$ by a predetermined mixing ratio, with $N_2$ being used as a balance.

As shown in FIG. 5, the material rich in the 2212 phase maintained the sensitivity after the lapse of 100 hours, without showing any deterioration. Whereas, the multi-system material showed unsatisfactory durability. In other words, in the case of the single-phase material, there is observed substantially no span drift (i.e. sensitivity change due to aging). As for the zero-point drift (i.e. change in the base resistance value due to aging), no drift was observed in the single-phase material, whereas the drift tended to occur in the multi-system material.

The zero-point drift characteristics are summarized in following Table 1. Here, it is understood that the rate of change in the resistance value comprises a rate between an initial resistance value for a base gas containing no NO and a resistance value for the base gas measured after the 1000 hour exposure of the material.

TABLE 1

|  | single-phase | multi-system |
| --- | --- | --- |
| rate of change in resistance value | 1.0 (no drift) | 1.6 (drift) |

As demonstrated above, the oxide compound, i.e. the single-phase material, obtained by employing the sintering temperature range specified above showed superior durability to the multi-system material. Further, of this material having the composition represented by the formula 6 and comprised mainly of the 2212 phase, when this material was provided also with a crystal size, as determined by the Wilson method, greater than 100 Å, there was observed excellent durability in a durability test conducted over a still longer period of time. For obtaining such excellent durability, it is then assumed that it is preferred for the crystal size to be greater than 100 Å. But, it was experimentally confirmed further that such excellent durability is generally available for those materials having the crystal size ranging between 100 Å and 650 Å. The reason why the confirmation was done for this particular size range is that the Wilson method provides significant values only for crystal sizes smaller than 1000 Å.

According to a further aspect of the present invention, there is provided a nitrogen oxide sensor which is superior not only in the aspects of the sensitivity to nitrogen oxide and reversible sensitivity but also in the other important sensor requirement of the durability (i.e. good resistance against sensitivity variation due to aging), the sensor comprising: a gas detecting portion formed of sensor material having electrical property thereof variable in response to concentration of a nitrogen oxide present in an atmosphere and electrodes electrically connected to the gas detecting portion;

wherein the senser material forming the gas detecting portion is comprised mainly of oxide compound having a composition represented by:

$$Bi_2Sr_2YCu_2O_{8+y} \quad \text{(formula 8)}$$

$(0 \leq y \leq 1)$ and having the 2212 phase.

The composition of the oxide compound and the role of the 2212 phase as its preferred crystal structure have already been described in connection with the method of the invention. Hence, this sensor has superior sensitivity to nitrogen oxides, reversible sensitivity as well as superior durability against aging.

Preferably, the gas detecting portion further includes inactive metal oxide which does not chemically react to the nitrogen oxide. With this, the physical strength of the gas detecting portion may be improved. Here, the 'inactive metal oxide' refers to metal oxide which does not irreversibly react with nitrogen oxide in any manner, especially chemically, such as $SiTiO_3$, $MgO$, $Al_2O_3$ and so on.

More preferably, the gas detecting portion mounts thereon an oxidation catalyst having platinum group element carried on a surface of the detecting portion. With this, the selectivity to nitrogen oxide may be further improved.

The above discussion concerns a nitrogen oxide sensor. Yet, the material employed as the sensor material in the nitrogen oxide sensor of the invention is assumed to have a catalytic ability on NOx-related chemical reaction. Then, it is preferred that this material be manufactured by the method of the present invention described hereinbefore.

Further and other objects, features and effects of the invention will become more apparent from the following more detailed description of the embodiments of the invention with reference to the accompanying drawings.

DESCRIPTION OF THE PREFERRED EMBODIMENTS

First, the construction of the sensor, the manufacturing method and the characteristics of this sensor will be described in this mentioned order with reference to the accompanying drawings.

[1] sensor construction

Figure 6:
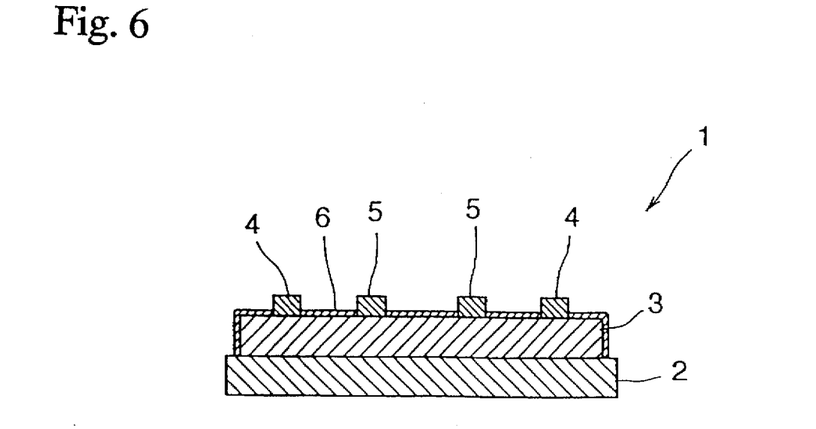
FIG. 6 is a schematic showing a construction of a nitrogen oxide sensor.

FIG. 6 shows a construction of a nitrogen oxide sensor according to the present invention. This sensor 1 includes a heating substrate 2 comprised of a ceramic heating plate and a gas detecting portion 3 mounted on the substrate 2 and formed of oxide compound. To this gas detecting portion 3, there are attached a pair of current-applying electrodes 4 made of platinum and a pair of potential detecting electrodes 5 made of platinum and corresponding respectively to the electrodes 4. The gas detecting portion 3 is provided in the form of a lump of material.

The composition of the gas detecting portion is as represented by the formula 6.

To the oxide compound forming the gas detecting portion, nitrogen oxide can be reversibly adsorbed, and presence/absence of nitrogen oxide adsorbed thereto causes the oxide compound to provide a different electric resistance value, which varies in proportion to the amount of the adsorbed nitrogen oxide, i.e. the concentration of the nitrogen oxide in the ambience gas. In this manner the gas detecting portion formed of the oxide compound provides a nitrogen oxide sensor.

[2] manufacturing method of the sensor (1) manufacturing method of the gas detecting portion 3:

The manufacturing method of the oxide compound forming the gas detecting portion 3 includes the following steps:

(first step)

for obtaining, from raw material powder mixture, a precursor containing components for constituting the sensor material in a predetermined equivalent ratio.

In the above, as the oxide compound has the above-described composition, the precursor is obtained by the mixing of metal elements (Bi:Sr:Y:Cu) so as to obtain substantially a predetermined equivalent ratio (2:2:1:2) among the components. The specific raw materials containing the respective metal elements are $Bi_2O_3$, $SrCO_3$, $Y_2O_3$, CuO and so on.

(second step)

for obtaining a preliminary sintered material by subjecting the precursor obtained from the first step to a preliminary sintering.

In this preliminary sintering step, the precursor is sintered for a period longer than 24 hours, preferably about 48 hours at a lower temperature (780° to 800° C. approximately) than a sintering temperature of a main sintering step (third step) to be described later.

This preliminary sintered product is ground and adjusted to a particle diameter of 1 to 20 μm approximately.

(third step)

subjecting the preliminary sintered material resulting from the second step to at least two cycles of main sintering step at 815° to 848° C. (T1) in a rare gas or nitrogen gas atmosphere containing 20% or more of oxygen, with an intermediate grinding step of the sintered material therebetween, thus obtaining the gas detecting portion 3 comprised mainly of oxide compound having a composition represented by:

$$Bi_2Sr_2YCu_2O_{8+y}$$ (formula 9)

$(0 \leq y \leq 1)$ and having 2212 phase.

In the intermediate grinding step, the sintered product is adjusted to a particle diameter of 1 to 20 μm approximately.

As the sintering atmosphere, rare gas such as argon gas, helium gas or nitrogen gas is employed. The main sintering is effected for at least two cycles, each cycle extending longer than 24 hours.

Preferably, the main sintering step is effected for at least two cycles each extending longer than 30 hours at a temperature range between 820° and 845° C. (T2) in argon gas atmosphere containing 20% or more of oxygen. The sintering temperature range should more preferably be between 828° and 835° C.

(2) manufacturing method of the sensor

The electrodes 4, 5 are attached on the gas detecting portion 3 obtained as above and the heating substrate 2 is attached to the lower side of the gas detecting portion 3. Then, the electrodes and the heating substrate are respectively connected to a measuring device and a controller (neither shown), thus forming the sensor. Further, when necessary, an oxidation catalyst 6 carrying a platinum element is attached to the surface of the gas detecting portion 3, as shown in FIG. 6.

(3) measurement of characteristics of the sensor

The measurement of the sensing characteristics of the nitrogen oxide sensor manufactured as above will be effected as follows.

A predetermined potential is applied to the heating substrate 2 and the gas detecting portion 3 is heated to 250° C. Also, a predetermined current is applied to the current electrodes 4. Under these conditions, the sensor is exposed to a gas containing a predetermined concentration of nitrogen oxide in the air. Then, a potential developed across the potential detecting electrodes is measured, and based on this, a change in the electric resistance value occurred at the gas detecting portion is determined.

[experiments]

Next, specific experiments will be described.

[1] manufacture of the gas detecting portion

The oxide compound for forming the gas detecting portion was manufactured according to the following steps.

A precursor was obtained by mixing powderly starting materials of $Bi_2O_3$, $SrCO_3$, $Y_2O_3$, CuO in such a manner as to obtain substantially a predetermined equivalent ratio (2:2:1:2). Then, this precursor was subjected to a 48-hour preliminary sintering step at a lower temperature: 790° C. than a sintering temperature of a main sintering step to be described later. This preliminary sintered product then was subjected to two cycles of the main sintering step in each of which the product was sintered at the predetermined elevated temperature (830° C.) for 30 hours. Incidentally, before these sintering steps, the precursor was mixed in advance with $SiTiO_3$ which functions as a binder between the particles.

By the X-ray diffraction method, it was confirmed that the crystal structure of the resultant oxide compound consisted mainly of the 2212 phase. FIG. 2 shows the c-axis length of this oxide compound together with those of comparison-sample oxide compounds which had the Y/Ca ratios of: 0.0/1.0, 0.8/0.2, and 0.9/0.1, respectively. As shown, in the equivalent ratio of 0.8 to 1.0 relating to the present invention, the c-axis length decreases substantially monotonously from about 30.30 to 30.02 Å. Accordingly, it is believed that the target material of the formula 6 was reliably obtained by the above-described procedure. The values of the c-axis length were calculated from the results of the X-ray diffraction analysis.

[3] characteristics of the sensor

The sensing characteristics of the nitrogen oxide sensor manufactured in the above-described manner were measured by the afore-described method.

Namely, a predetermined potential was applied to the heating substrate 2 and the gas detecting portion 3 was heated to 250° C. Also, a predetermined current was applied to the current electrodes 4. Under these conditions, the sensor was exposed to a gas containing a predetermined concentration of nitrogen oxide in the air. Then, a potential developed across the potential detecting electrodes was measured, and based on this, a corresponding change in the electric resistance value occurred at the gas detecting portion 3 was determined.

As described above, the detection-subject gas was air containing 2500 ppm of NO as a nitrogen oxide. The results are shown in FIG. 1. This FIG. 1 also shows, for comparison, the experiment results of the other gas detecting portions comprised of the oxide compound the Y/Ca ratios of: 0.0/1.0, 0.2/0.8, 0.4/0.6, 0.6/0.4, 0.8/0.2 and 0.9/0.1, respectively. The figure clearly demonstrates the superiority of the sensor of the present invention having the gas detecting portion comprised of the oxide compound having the composition: Y/Ca=1.0/0.0.

Figure 7:
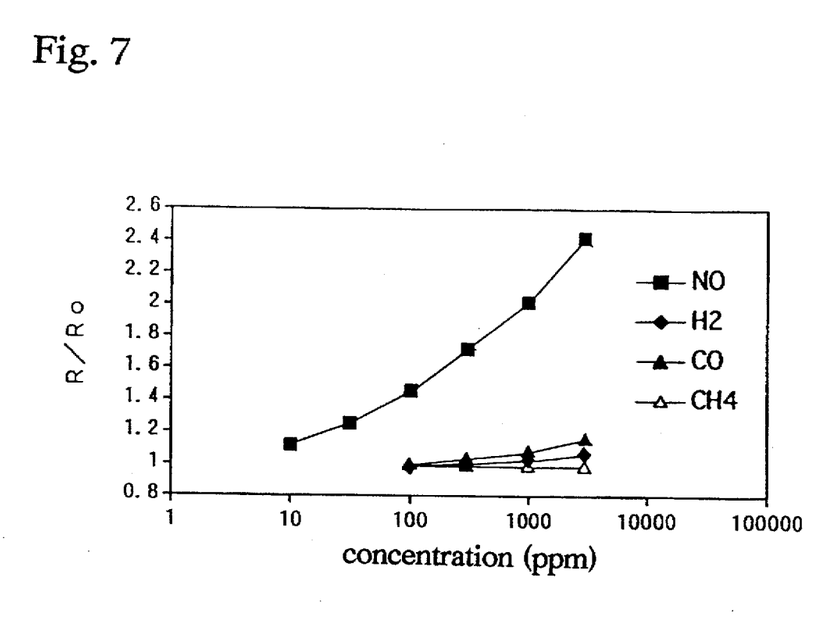
FIG. 7 is graph illustrating the sensing characteristics of the sensor.

FIG. 7 illustrates the selectivity of the above sensor for the target nitrogen oxide against other non-target gas component (hydrogen, carbon monoxide, methane). This figure demonstrates that this sensor has sufficient selectivity for NO against the other disturbing gas components. In this figure, the kinds of gas components are denoted by graphic marks.

The invention may be embodied in other specific forms without departing from the spirit or essential characteristics thereof. The present embodiments are therefore to be considered in all respects as illustrative and not restrictive, the scope of the invention being indicated by the appended claims rather than the foregoing description and all changes which come within the meaning and range of equivalency of the claims are therefore intended to be embraced therein.

What is claimed is:

1. A method of manufacturing a nitrogen oxide sensor having a gas detecting portion formed of sensor material having electrical property thereof variable in response to concentration of nitrogen oxide present in an atmosphere and electrodes electrically connected to the gas detecting portion, the method comprising:

a first step of obtaining a precursor containing components for constituting the sensor material in a predetermined equivalent ratio of stoichiometry between chemical elements;

a second step of obtaining a preliminary sintered material by subjecting the precursor obtained from the first step to a preliminary sintering; and a third step of subjecting the preliminary sintered material resulting from the second step to at least two cycles of main sintering step at 815° to 848° C. (T1) with an intermediate grinding step of the sintered material therebetween, thus obtaining the gas detecting portion comprised mainly of oxide compound having a composition represented by:

$$Bi_2Sr_2YCu_2O_{8+y} \qquad \text{(formula 1)}$$

$(0 \leq y \leq 1)$
and having the 2212 phase of crystal structure.

2. A method according to claim 1, wherein the main sintering step is effected for at least two cycles at a more-focused temperature range of 820° to 845° C. (T2) for a period longer than 30 (thirty) hours in each cycle.

3. A nitrogen oxide sensor having a gas detecting portion formed of sensor material having electrical property thereof variable in response to concentration of a nitrogen oxide present in an atmosphere and electrodes electrically connected to the gas detecting portion;

wherein the senser material forming the gas detecting portion is comprised mainly of oxide compound having a composition represented by:

$$Bi_2Sr_2YCu_2O_{8+y} \qquad \text{(formula 2)}$$

$(0 \leq y \leq 1)$
and having the 2212 phase of crystal structure; and the sensor material is manufactured by a method comprising:

a first step of obtaining a precursor containing components for constituting the sensor material in a predetermined equivalent ratio according to the stoichiometry between chemical elements of formula 2;

a second step of obtaining a preliminary sintered material by subjecting the precursor obtained from the first step to a preliminary sintering; and a third step of subjecting the preliminary sintered material resulting from the second step to at least two cycles of main sintering step at 815° to 848° C. (T1) with an intermediate grinding step of the sintered material therebetween.

4. A nitrogen oxide sensor according to claim 3, wherein the gas detecting portion further includes inactive metal oxide which does not chemically react to the nitrogen oxide.

5. A nitrogen oxide sensor according to claim 3 or 4, wherein the gas detecting portion mounts thereon an oxidation catalyst having platinum group element carried at least on a surface of the detecting portion.

6. A method of manufacturing material comprising:

a first step of obtaining a precursor containing components for constituting the sensor material in a predetermined equivalent ratio of stoichiometry between chemical elements;

a second step of obtaining a preliminary sintered material by subjecting the precursor obtained from the first step to a preliminary sintering; and a third step of subjecting the preliminary sintered material resulting from the second step to at least two cycles of main sintering step at 815° to 848° C. (T1) with an intermediate grinding step of the sintered material therebetween, thus obtaining the material comprised mainly of oxide compound having a composition represented by:

$$Bi_2Sr_2YCu_2O_{8+y} \qquad \text{(formula 3)}$$

$(0 \leq y \leq 1)$
and having the 2212 phase of crystal structure.

* * * * *